(12) United States Patent
Ogawa et al.

(10) Patent No.: US 7,563,927 B2
(45) Date of Patent: Jul. 21, 2009

(54) PROCESS FOR PRODUCING (METH)ACRYLIC ACID OR (METH)ACROLEIN

(75) Inventors: Yasushi Ogawa, Mie (JP); Shuhei Yada, Mie (JP); Yoshiro Suzuki, Mie (JP); Kenji Takasaki, Mie (JP); Kimikatsu Jinno, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 210 days.

(21) Appl. No.: 11/547,004

(22) PCT Filed: Oct. 27, 2004

(86) PCT No.: PCT/JP2004/016292

§ 371 (c)(1),
(2), (4) Date: Dec. 19, 2006

(87) PCT Pub. No.: WO2005/100293

PCT Pub. Date: Oct. 27, 2005

(65) Prior Publication Data

US 2007/0208201 A1      Sep. 6, 2007

(30) Foreign Application Priority Data

Apr. 1, 2004    (JP) .............................. 2004-108736

(51) Int. Cl.
*C07C 51/16* (2006.01)
(52) U.S. Cl. ...................... 562/532; 562/534; 562/535
(58) Field of Classification Search ................. 562/549, 562/532, 534, 535
See application file for complete search history.

(56) References Cited

U.S. PATENT DOCUMENTS

| 7,094,921 B2 | 8/2006 | Yada et al. |
| 2004/0204608 A1 | 10/2004 | Yada et al. |
| 2006/0211886 A1 | 9/2006 | Yada et al. |

FOREIGN PATENT DOCUMENTS

JP        54 21966        2/1979

(Continued)

OTHER PUBLICATIONS

U.S. Appl. No. 11/547,864, filed Oct. 6, 2006, Ogawa, et al.

(Continued)

*Primary Examiner*—Taylor Victor Oh
(74) *Attorney, Agent, or Firm*—Oblon, Spivak, McClelland, Maier & Neustadt, P.C.

(57)      ABSTRACT

A producing method of (meth)acrolein or (meth)acrylic acid where by use of a multi-tubular reactor that has a plurality of reaction tubes filled with a catalyst, catalytic gas phase oxidation of propylene, propane, isobutylene or (meth)acrolein is carried out in the presence of a composite oxide catalyst by use of molecular oxygen or a gas containing molecular oxygen, in which method (meth)acrolein or (meth)acrylic acid can be obtained stably in high yield for a long period of time without allowing the activity of the catalyst to decrease locally (disproportionately) and extremely. A temperature difference between a temperature of a heat medium at the beginning of operation and a peak temperature of the catalyst is set in a range of 20 to 80° C., and during operations a change of the peak temperature T of the catalyst in a tube axis direction is maintained in a definite range.

20 Claims, 3 Drawing Sheets

FOREIGN PATENT DOCUMENTS

| | | |
|---|---|---|
| JP | 8 92147 | 4/1996 |
| JP | 2000 53610 | 2/2000 |
| JP | 2004 83430 | 3/2004 |
| WO | 01 42184 | 6/2001 |
| WO | 03 055835 | 7/2003 |

OTHER PUBLICATIONS

U.S. Appl. No. 11/587,990, filed Oct. 30, 2006, Jinno, et al.
U.S. Appl. No. 11/547,004, filed Oct. 2, 2006, Ogawa, et al.
U.S. Appl. No. 11/451,355, filed Jun. 13, 2006, Yada, et al.

PROCESS FOR PRODUCING (METH)ACRYLIC ACID OR (METH)ACROLEIN

TECHNICAL FIELD

The present invention relates to a producing method where at least one kind of substance to be oxidized of propylene, propane, isobutylene and (meth)acrolein is catalytically oxidized in a gas phase with molecular oxygen to form (meth) acrolein or (meth)acrylic acid stably and efficiently.

BACKGROUND ART

In general, (meth)acrylic acid or (meth)acrolein is continuously produced in such a manner that, by use of a multi-tubular reactor having a plurality of reaction tubes in each of which a catalyst is packed, propylene, propane, isobutylene or (meth)acrolein that is a substance to be oxidized is catalytically oxidized with molecular oxygen or molecular oxygen-containing gas in a gas phase in the presence of a composite oxide catalyst.

In the reaction tubes, a temperature distribution is generated in a direction of a flow (in a tube axis direction) of a process gas consisting of a substance to be oxidized and molecular oxygen or a molecular oxygen-containing gas. In general, a temperature peak exists on an upstream side.

FIG. 3 shows a change in a temperature distribution in the tube axis direction resulting from a continuous operation. As an operation is continued, the activity of a catalyst deteriorates and particularly a decrease in the activity of the catalyst is large in the upstream side. Accordingly, a reaction velocity in the region declines to result in a decrease in a heat release value owing to a reaction. Concerning the flow of the gas on a more downstream side than there, as a reaction amount on the upstream side decreases, since a concentration of a raw material that is supplied becomes higher, a reaction amount increases and a heat release value increases. However, a total reaction amount over an entire reaction tube decreases. At this time, a position of a temperature peak in a tube axis direction (hereinafter, referred to as a peak position) moves toward a downstream side and a peak temperature declines (a temperature distribution varies from a to b). To the situation, so far an operation is carried out in such a manner that a temperature of a heat medium (reaction temperature) is raised to bring the peak position back to the upstream side and to heighten a peak temperature, thereby improving the catalyst activity to maintain a yield (the temperature distribution changes from b to c').

DISCLOSURE OF THE INVENTION

The problem concerning the conventional operation is in that the change of the peak temperature from the beginning of the operation is so large that the load on the catalyst in the neighborhood of the peak position becomes heavy and the catalyst activity in the region is rapidly deteriorated. Accordingly, the temperature of the heat medium is raised to reactivate the catalyst activity, and thereby a decrease in the yield due to deactivation of the catalyst can be compensated for a short period. However, thereafter, after a definite time has passed, the catalyst activity extremely deteriorates locally, resulting in a rapid deterioration in the yield.

The present invention intends to provide a method of producing (meth)acrolein or (meth)acrylic acid in which method by use of a multi-tubular reactor having a plurality of reaction tubes in each of which a catalyst is packed, proplyene, propane, isobutylene or (meth)acrolein is catalytically oxidized in a gas phase with molecular oxygen or molecular oxygen-containing gas in the presence of a composite oxide catalyst, wherein (meth)acrolein or (meth)acrylic acid can be obtained stably, with high yield and without locally deactivating the catalyst.

The present inventors, after studying hard, found that when, in order to overcome the decrease in the catalyst activity caused by the continuous operation, without excessively raising the temperature of the heat medium to maintain the reaction yield, the peak temperature of the catalyst is moved within a definite range to the downstream side, with the local deactivation of the catalyst avoiding, (meth)acrolein or (meth)acrylic acid can be obtained stably and with high yield, and came to the present invention.

In other words, according to the invention, the following producing method of (meth)acrolein or (meth)acrylic acid is provided, and thereby the object of the invention mentioned above can be achieved.

That is a method in which (meth)acrylic acid or (meth) acrolein is produced by use of a fixed bed multi-tubular reactor that has a structure that has a plurality of reaction tubes provided with at least one catalyst layer in a tube axis direction and allows a heat medium for controlling a reaction temperature to flow outside of the reaction tubes, in the reaction tubes, gas phase catalytic oxidation between at least one kind of substance to be oxidizes of propylene, propane, isobutylene, and (meth)acrolein and molecular oxygen or a gas containing molecular oxygen is carried out, characterized in that, at the beginning of operation, temperature difference between a temperature of the heat medium and a peak temperature of the catalyst is set in the range of 20 to 80 C., and during operations a peak temperature T (° C.) of the catalyst in a tube axis direction satisfies an equation 1 below.

$$35 \leq L \times \left( \frac{|T - T_0|}{X - X_0} \right) \leq 300 \qquad \text{(Equation 1)}$$

(In the equation 1, L, $T_0$, X, and $X_0$, respectively, denote a length of a reaction tube, a peak temperature of a catalyst in a tube axis direction at the beginning of operation, a length up to a position that shows the peak temperature T from an entrance of the reaction tube and a length up to a position that shows the peak temperature $T_0$ from the entrance of the reaction tube.)

Figure 1:
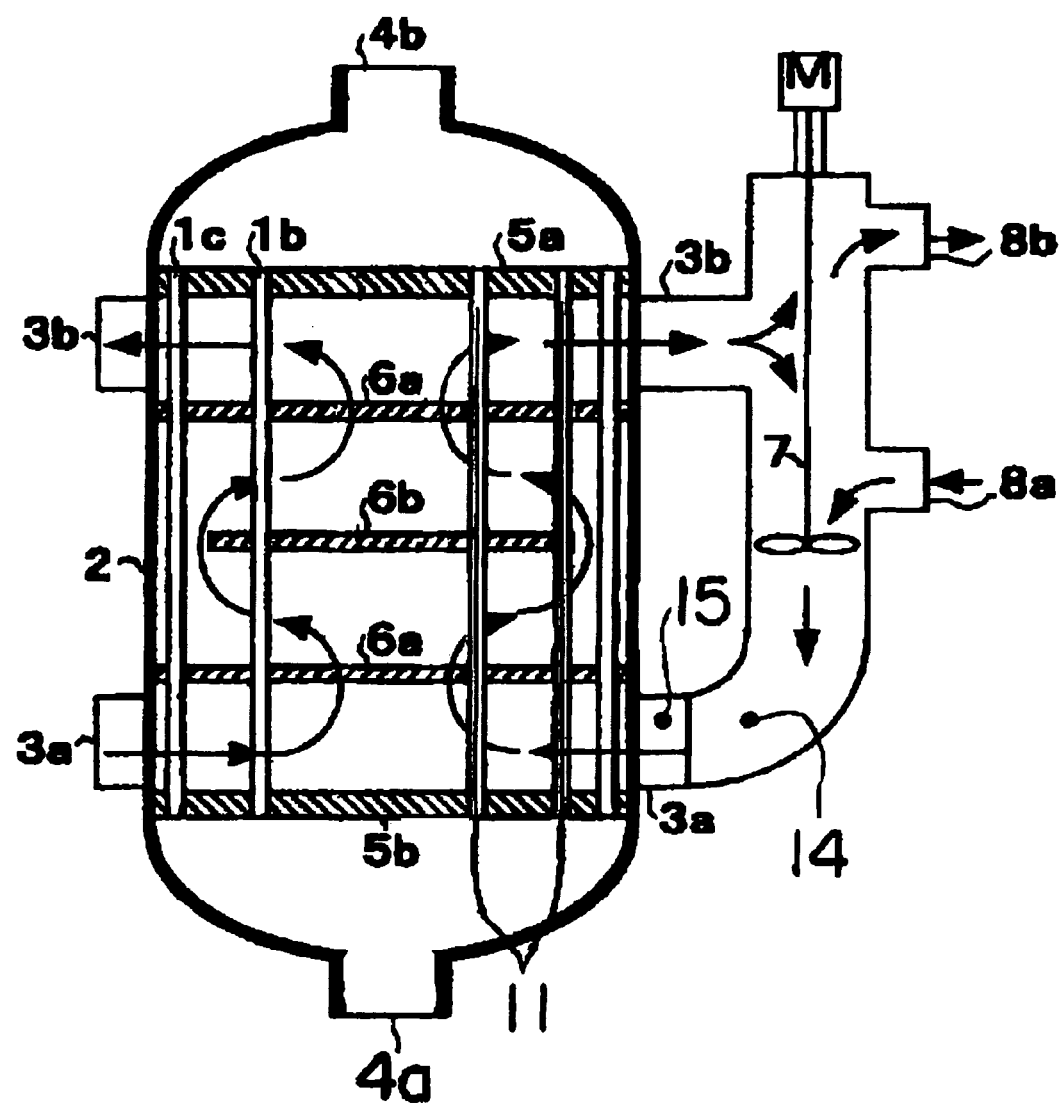
FIG. 1 is a schematic cross-sectional view of one embodiment of a multi-tubular heat exchange type reactor used for the gas phase catalytic oxidation method according to the present invention.

In the drawings, reference numerals 1b and 1c each denotes a reaction tube; 2, a reactor; 3a and 3b each, a circular conduit pipe; 3a' and 3b' each, a circular conduit pipe; 4a, a product exhaust exit; 4b, a raw material supply port; 5a and 5b each, a tube plate; 6a and 6b each, a baffle plate with a window; 6a' and 6b' each, a baffle plate with a window; 7, a circulation pump; 8a and 8a' each, a heat medium supply line; 8b and 8b' each, a heat medium discharge line; 11, 14 and 15 each, a thermometer; reference signs a, b, c and c' each, a temperature distribution; $X_1$, an entrance position of the reaction tube (process gas entrance); and $X_2$, an exit position of the reaction tube (process gas exit).

BEST MODE FOR CARRYING OUT THE INVENTION

In what follows, the present invention will be detailed.

The present invention is a method where by use of a fixed bed multi-tubular reactor that has a structure that has a plurality of reaction tubes provided with at least one catalyst layer in a tube axis direction and allows a heat medium for controlling a reaction temperature to flow outside of the reaction tubes, in the reaction tubes, gas phase catalytic oxidation between at least one kind of substance to be oxidized of propylene, propane, isobutylene, and (meth)acrolein and molecular oxygen or a gas containing molecular oxygen is carried out to produce (meth)acrylic acid or (meth)acrolein continuously.

Temperature difference at the beginning of operation between a temperature of the heat medium and a peak temperature of the catalyst is set in the range of 20 to 80° C., and preferably in the range of 20 to 70° C. The temperature of the heat medium mentioned above is a temperature at an entrance from which the heat medium is supplied to the reactor. When, at the beginning of operation, the temperature of the heat medium is controlled so as to set the temperature difference with the peak temperature of the catalyst to be in the above range, in the reaction tubes, localization of an exothermal reaction can be suppressed. As a result, the activity of the catalyst can be inhibited from locally deteriorating largely. This is observed as a phenomenon in which in a temperature distribution of the catalyst with respect to a direction in which a process gas flows (in a tube axis direction) a shape of the peak temperature existing in an upstream side does not locally protrude and a transition to a downstream side as well as a decrease in the peak temperature diminishes while the operation is continued.

An actual temperature difference between the observed peak temperature mentioned above and the temperature of the heat medium at the beginning of operation is preferably in the range of 20 to 80° C., and more preferably in the range of 20 to 70° C.

Even when the temperature of the heat medium is set as above stated at the beginning of operation, with continuation of the operation, a decrease in a peak temperature caused by a decrease in the activity of the catalyst and a transition of a peak position cannot be avoided. Accordingly, in the invention, during operation, the peak temperature T (° C.) of the catalyst in a tube axis direction is made to satisfy an equation 1, and preferably an equation 2 below. In this case, when the temperature of the heat medium is changed, the peak temperature T can be controlled, and, specifically, when the temperature of the heat medium is raised, the peak temperature T can be raised and the peak position can be moved to the upstream side.

$$35 \leq L \times \left(\frac{|T - T_0|}{X - X_0}\right) \leq 300 \quad \text{(Equation 1)}$$

$$40 \leq L \times \left(\frac{|T - T_0|}{X - X_0}\right) \leq 200 \quad \text{(Equation 2)}$$

(In the equation 1, L, $T_0$, X, and $X_0$, respectively, denote a length of a reaction tube (unit: mm), a peak temperature of a catalyst in a tube axis direction at the beginning of operation (unit: ° C.), a length from an entrance of the reaction tube up to a position that shows the peak temperature T (unit: mm) and a length from the entrance of the reaction tube up to a position that shows the peak temperature $T_0$ (unit: mm)).

In the case that $L \times \{|T-T_0|/(X-X_0)\}$ is too big, a change of the position of the peak temperature is so small to cause the localization of a deactivation region of the catalyst. Accordingly, it is not desirable that $L \times \{|T-T_0|/(X-X_0)\}$ is more than 300. On the contrary, when $L \times \{|T-T_0|/(X-X_0)\}$ is too small, the localization of the deactivation of the catalyst can be avoided, however, as the total reaction amount decreases, it is not desirable that $L \times \{|T-T_0|/(X-X_0)\}$ becomes less than 35.

Figure 2:
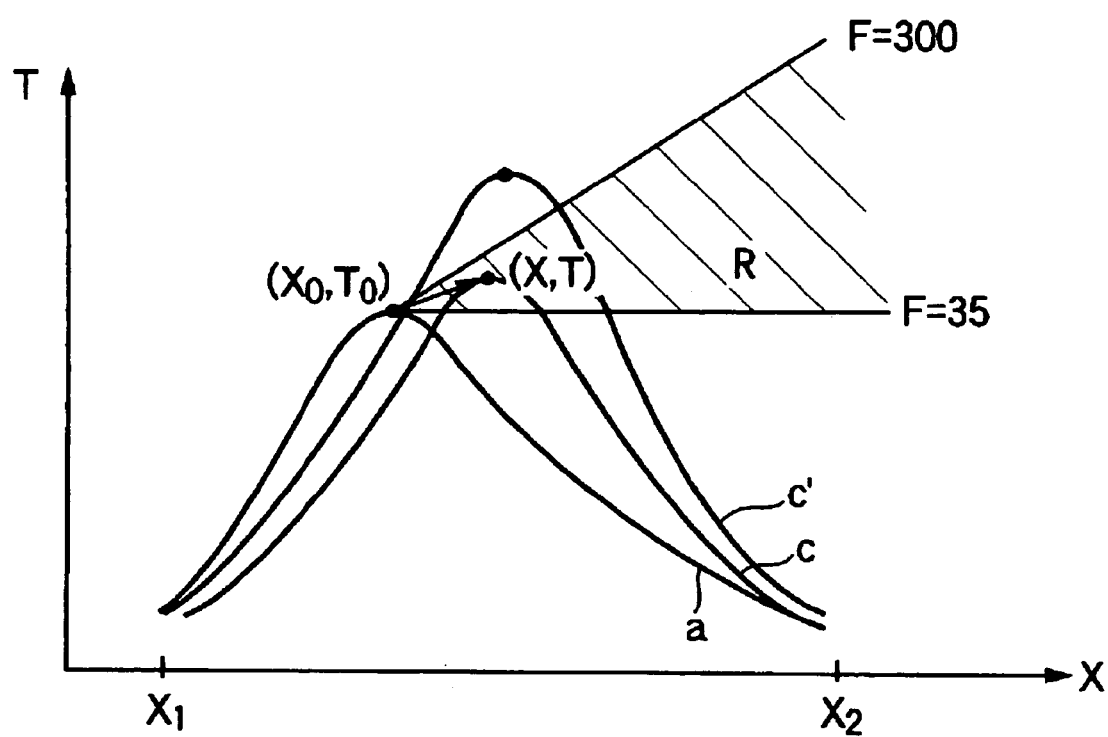
FIG. 2 is a diagram showing a change of a temperature distribution, caused by continuous operation, in a tube axis direction of the reactor tube of the invention.
Figure 3:
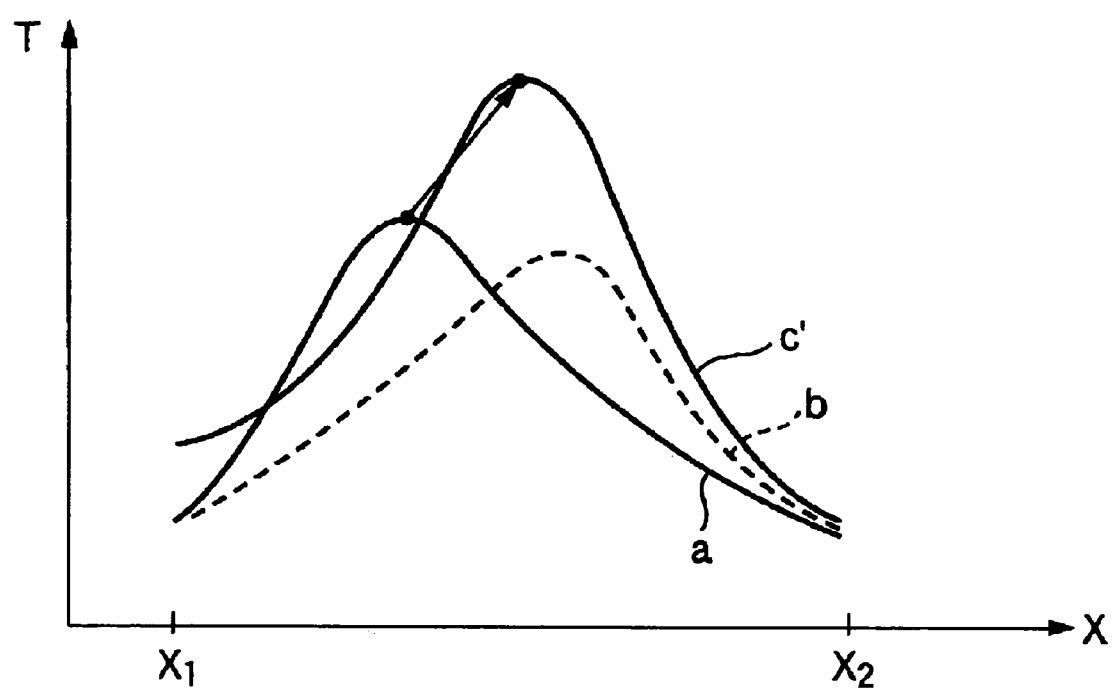
FIG. 3 is a diagram showing a change of a temperature distribution, caused by the continuous operation, in a tube axis direction of the reactor tube.

In FIG. 2, a change of the temperature distribution of the catalyst in a tube axis direction when the peak temperature T satisfies the equation 1 in the continuous operation is shown. That the peak temperature T satisfies the equation 1 means that, in FIG. 2, a range in which the peak temperature T moves is in a definite range (in the region R). For example, a temperature distribution a at the beginning of operation is changed to a temperature distribution c as the operation goes on.

In this way, when the peak temperature T is controlled so as to be in a definite range during the operation, the change of the peak temperature T can be made smaller, that is, by avoiding a concentration of the load on the catalyst having the decreased activity, thereby the activity of catalyst can be suppressed from locally decreasing. Accordingly, for a long time, (meth)acrylic acid or (meth)acrolein can be stably produced with high yield.

In order to make the peak temperature T during operation satisfy the equation 1, it is desirable to control the peak temperature T so that the difference between the peak temperature T and a temperature of the heat medium may be preferably in the range of 20 to 80° C., and more preferably in the range of 20 to 70° C.

In what follows, a reaction method, a reactor, a catalyst and so on that are used to produce (meth)acrylic acid or (meth)acrolein by a gas phase catalytic oxidation of raw materials will be explained.

Recently, amounts of production of acrylic acid from propylene and of methacrylic acid from isobutylene (they are called collectively (meth)acrylic acid) are rapidly expanding with an increase in the demands thereof. Accordingly, many plants are built all over the world and a scale of production of each plant has been enlarged to one hundred thousand tons or more per year. Enlargement of the scale of production of the plant is the reason for necessity to enlarge an amount of production of each oxidation reactor. Accordingly, a load on a gas phase catalytic oxidation reactor used for propane, propylene, or isobutylene and a catalyst used has become heavy. In connection with this, an operational condition that can maintain stability of the catalyst under a heavy load is in demand.

In the invention, a method in which with a multi-tubular reactor that includes a cylindrical reactor shell having a raw material supply port and a product discharge port; a plurality of circular conduits that is disposed outside of the cylindrical reactor shell and used to introduce or take a heat medium in or out of the cylindrical reactor shell; circular devices connecting the plurality of circular conduits each other; a plurality of reaction tubes that is restrained by a plurality of tube plates of the reactor and contains a catalyst; and a plurality of baffle plates for altering a direction of a heat medium introduced in the reactor shell in a longer direction of the reaction tube, a substance to be oxidized is oxidized with a molecular oxygen-containing gas according to gas phase catalytic oxidation is adopted, in the reaction tubes, an oxidation catalyst such as a Mo—Bi-based catalyst and/or a Mo—V-based catalyst being filled.

The invention is a gas phase catalytic oxidation method in which propylene, propane, isobutylene or (meth)acrolein or a mixture thereof as a substance to be oxidized is catalytically oxidized in gas phase with a molecular oxygen-containing gas to obtain (meth)acrolein or (meth)acrylic acid. From propylene, propane, and isobutylene, (meth)acrolein, (meth)acrylic acid or both thereof can be obtained. Furthermore, from (meth)acrolein, (meth)acrylic acid is obtained.

In the invention, a "process gas" means a gas involving the gas phase catalytic oxidation such as a substance to be oxidized as a raw material gas, a gas containing molecular oxygen, and a product obtained. A "raw material" is synonymous with a substance to be oxidized.

(Composition of Raw Material Gas)

In a multi-tubular reactor used for the gas phase catalytic oxidation, a gas mixture of at least one kind of substance to be oxidized of propylene, propane, isobutylene, and (meth)acrolein as a raw material gas, a gas containing molecular oxygen and water vapor is mainly introduced into the reactor.

In the invention, a concentration of a substance to be oxidized in a mixed gas is in a range of 6 to 10 mole %, that of oxygen is in a range of 1.5 to 2.5 mole times the concentration of the substance to be oxidized, and that of water vapor is in a range of 0.8 to 5 mole times. The mixed gas introduced is divided into each reaction tube, goes through the reaction tube, and reacts in the presence of an oxidation catalyst filled in the tube.

(Multi-Tubular Reactor)

A gas phase catalytic oxidation according to the invention that uses a fixed bed multi-tubular reactor is widely used when from at least one kind of substance to be oxidized of propylene, propane, isobutylene and (meth)acrolein, in the presence of a composite oxide catalyst, by use of molecular oxygen or a gas containing molecular oxygen, (meth)acrylic acid or (meth)acrolein is produced.

The fixed bed multi-tubular reactor for use in the invention is one widely used industrially, and there is no particular restriction on it.

A reactor or the like that can be used in the method of the invention will be explained with reference to FIG. 1.

(FIG. 1)

FIG. 1 is a schematic cross sectional view showing one embodiment of a multi-tubular heat exchange type reactor that is used in a gas phase catalytic oxidation method according to the invention.

To a shell 2 of the multi-tubular reactor, reaction tubes 1b and 1c are arranged fixed to the tube plates 5a and 5b. A raw material supply port from which a raw material gas is introduced and a product discharge port from which a product goes out are shown with 4a or 4b. When a flow of the process gas and that of the heat medium are in a counter current flow, there is no particular restriction on a flow direction of the process gas. However, in FIG. 1, because the flow direction of the heat medium in the reactor shell is shown as a climbing flow with an arrowhead, 4b denotes the raw material supply port. At an outer periphery of the reactor shell, a circular conduit 3a is arranged to introduce the heat medium. The heat medium that is pressurized by the circulation pump 7 of the heat medium goes up from the circular conduit 3a inside of the reactor shell. By arranging each of a plurality of baffle plates 6a having windows near the center of the reactor shell and each of a plurality of baffle plates 6b having a window at the outer periphery of the reactor shell in an alternate manner, the flow direction is changed and the heat medium returns from the circular conduit 3b to the circular pump. Part of the heat medium that has absorbed the reaction heat goes out from a discharge pipe disposed at a top portion of the circular pump 7, is cooled with a heat exchanger (now shown in the drawing), and is introduced again from a heat medium supply line 8a into the reactor. A temperature of the heat medium is controlled when either a temperature or a flow rate of a refluxed heat medium introduced from the heat medium supply line 8a is controlled to control a thermometer 14.

The temperature control of the heat medium is, though depending on the performance of the catalyst used, carried out so that difference of temperatures of the heat medium in the heat medium supply line 8a and the heat medium in the heat medium discharge line 8b may be in the range of 1 to 10° C., and preferably in the range of 2 to 6° C.

Thermometers 11 are inserted into the reaction tubes arranged in the reactor, signals are transmitted outside of the reactor, and thereby a temperature distribution of the catalyst layer in tube axis direction of the reactor is recorded. A thermometer is inserted in each of a plurality of the reaction tubes, and with one thermometer, in a tube axis direction, normally, at 5 points and more, preferably at 10 points and more, and more preferably at 20 points and more, temperatures are observed. A thermometer that has a variable temperature measurement portion and can measure at infinite points may be used.

(Catalyst)

As a catalyst used for a gas phase catalytic oxidation to generate (meth)acrylic acid or (meth)acrolein, there are ones that are used in a first half of the reaction where olefin is converted into unsaturated aldehyde or unsaturated acid and ones that are used in second half of the reaction where unsaturated aldehyde is converted into unsaturated acid.

In the gas phase catalytic oxidation reaction, as a Mo—Bi-based composite oxide catalyst that is used in the first half of the reaction mainly manufacturing acrolein (a reaction of converting olefin into unsaturated aldehyde or unsaturated acid), ones denoted by a general formula (I) below can be cited.

$$Mo_aW_bBi_cFe_dA_eB_fC_gD_hE_iO_x \qquad (I)$$

In the general formula (I), A, B, C, D, E, and O respectively denote at least one kind of element selected from nickel and cobalt, at least one kind of element selected from sodium, potassium, rubidium, cesium, and thallium, at least one kind of element selected from alkaline earth metals, at least one kind of element selected from phosphorous, tellurium, antimony, tin, cerium, lead, niobium, manganese, arsenic, boron and zinc, at least one kind of element selected from silicon, aluminum, titanium, and zirconium, and oxygen. Furthermore, a, b, c, d, e, f, g, h, i and x, respectively, denote atomic ratios of Mo, W, Bi, Fe, A, B, C, D, E, and O, and in the case of a=12, $0 \leq b \leq 10$, $0 < c \leq 10$ (preferably $0.1 \leq c \leq 10$), $0 < d \leq 10$ (preferably $0.1 \leq d \leq 10$), $2 \leq e \leq 15$, $0 < f \leq 10$ (preferably $0.001 \leq f \leq 10$), $0 \leq g \leq 10$, $0 \leq h \leq 4$, and $0 \leq i \leq 30$, and x denotes a value determined by the oxidation state of the respective elements.

In the gas phase catalytic oxidation, as a Mo—V-based composite oxide catalyst used in a the second half thereof where acrolein is oxidized into acrylic acid (a reaction from unsaturated aldehyde to unsaturated acid), ones denoted by a general formula (II) below can be cited.

$$Mo_aV_bW_cCu_dX_eY_fO_g \quad (II)$$

In the general formula (II), X, Y, and O, respectively, denote at least one kind of element selected from Mg, Ca, Sr, and Ba, at least one kind of element selected from Ti, Zr, Ce, Cr, Mn, Fe, Co, Ni, Zn, Nb, Sn, Sb, Pb, and Bi, and oxygen. Furthermore, a, b, c, d, e, f, and g, respectively, denote atomic ratios of Mo, V, W, Cu, X, Y, and O, and in the case of a=12, $2 \leq b \leq 14$, $0 \leq c \leq 12$, $0 < d \leq 6$, $0 \leq e \leq 3$, $0 \leq f \leq 3$, and g is a value determined by oxidation states of the respective elements.

The catalysts mentioned above are manufactured according to methods disclosed in JP-A-63-54942, JP-B-6-13096 and JP-B-6-38918.

In what follows, collateral items of the invention will be described.

(Step of Manufacturing Acrylic Acid)

As steps of manufacturing acrylic acid, steps (i) to (iii) below, for example, can be cited.

(i) an oxidation step where propane, propylene and/or acrolein are/is subjected to a gas phase catalytic oxidation, a catching step where acrylic acid-containing gas from the oxidation step is contacted to water so that acrylic acid is caught as an aqueous solution of acrylic acid and an extraction step where acrylic acid is extracted from the aqueous solution of acrylic acid using an appropriate extracting solvent are done, then acrylic acid is separated from the solvent, purification is conducted by a purification step and, further, a Michael adduct of acrylic acid and a high boiling point solution containing a polymerization inhibitor used in each step are supplied to a decomposition reaction tower as raw materials to recover valuables and the valuables are supplied to any of the steps after the catching step;

(ii) an oxidation step where propylene, propane and/or acrolein are/is subjected to a gas phase catalytic oxidation to produce acrylic acid, a catching step where acrylic acid-containing gas is contacted to water so that acrylic acid is caught as an aqueous solution of acrylic acid, an azeotropic separation step where the aqueous solution of acrylic acid is distilled in an azeotropic separation tower in the presence of an azeotropic solvent whereupon crude acrylic acid is taken out from the bottom of the tower and a step for separation of acetic acid where acetic acid is removed and a purification for high boiling point impurities are done, then a Michael adduct of acrylic acid after the purification and a high boiling point solution containing a polymerization inhibitor used for those production steps are supplied to a decomposition reaction tower as raw materials to recover the valuables and the valuables are supplied to any of the steps after the catching step; and (iii) an oxidation step where acrylic acid is produced by a gas phase catalytic oxidation of propylene, propane and/or acrolein, a catching/separation step where acrylic acid-containing gas is contacted to an organic solvent to catch acrylic acid as a solution of acrylic acid in the organic solvent whereby water, acetic acid, etc. are removed at the same time, a separation step where acrylic acid is taken out from the solution of acrylic acid in the organic solvent, a step where a high boiling point solution containing a Michael adduct of acrylic acid, organic solvent and polymerization inhibitor used in those production steps is supplied to a decomposition reaction tower as a raw material to recover the valuables and the valuables are supplied to any of the steps after the catching step and a step where the organic solvent is partially purified are done.

Thus obtained acrylic acid or acrylic acid esters whose raw material is the acrylic acid are used in various applications. Specifically, a super absorbent polymer, a coagulant, a pressure-sensitive adhesive, a coating medium, an adhesive, and a fiber modifier can be cited.

EXAMPLE

In what follows, the present invention will be specifically explained with reference to an example and a comparative example. However, the invention is not restricted to these.

(Catalyst)

Into 400 parts by weight of pure water, 94 parts by weight of ammonium paramolybdate were dissolved under heating. On the other hand, 7.2 parts by weight of ferric nitrate, 25 parts by weight of cobalt nitrate, and 38 parts by weight of nickel nitrate were dissolved in 60 parts by weight of pure water under heating. These solutions were mixed under thorough agitation and thereby a slurry-like solution was obtained.

Subsequently, 0.85 parts by weight of borax and 0.36 parts by weight of potassium nitrate were dissolved into 40 parts by weight of purified water under heating, followed by adding to the slurry. In the next place, 64 parts by weight of particulate silica were added followed by agitating. Then, thereto, 58 parts by weight of bismuth subcarbonate to which 0.8 weight % of Mg was beforehand compounded was added and agitated to blend. After the slurry was heated to dry, heat treatment was applied at a temperature of 300° C. for 1 hr in an air atmosphere. Thereafter, obtained particulate solid was molded into tablets having a diameter of 5 mm and a height of 4 mm by means of tablet compression using a molding machine, followed by sintering at a temperature of 500° C. for 4 hrs to obtain a catalyst for a first half process.

The obtained catalyst for first half process was a Mo—Bi-based composite oxide having a composition ratio of a catalyst powder with a composition of $Mo_{12}Bi_5Ni_3Co_2Fe_{0.4}Na_{0.2}Mg_{0.4}B_{0.2}K_{0.1}Si_{24}O_x$ (x is a value determined depending on oxidation states of the respective metals).

(Production of Acrylic Acid or Acrolein from Propylene)

In the present example, a multi-tubular reactor same as that shown in FIG. 1 was used.

Specifically, a multi-tubular reactor having 10,000 stainless steel-made reaction tubes having a length of 3.5 m and an inner diameter of 27 mm was used.

As a heat medium, molten salt of mixture of nitrates (niter) was used, supplied from a lower portion of the reactor and discharged from an upper portion thereof to circulate.

The heat medium was partially discharged from 8b to cool, followed by returning to 8a. Thereby, a temperature of the heat medium supplied to the reactor was controlled and the temperature thereof was measured by use of a thermometer 15.

As a catalyst that is filled in each reaction tube, one which was obtained by blending the catalyst for a first half process and silica-made balls that have no catalytic activity and a diameter of 5.5 mm at a volume ratio of 7:3 was filled so that a packing layer height in each reaction tube might be 2.9 m.

The raw material gas was supplied from the upper portion of the reactor so as to be a counterflow with respect to the heat medium, and at 60 kPa (gauge pressure) a raw material gas containing propylene at a concentration of 9.5 mol %, a molecular oxygen at a concentration of 14.5 mol %, water at 9.5 mol %, and nitrogen at 66.5 mol % (measuring interval: 80 mm on an upstream side and 240 mm on a downstream side) having 20 measurement points in a tube axis direction was inserted in each reaction tube to measure the temperature distribution.

Example

An operation was began by filling a catalyst produced newly in a way mentioned above in a reactor and supplying raw material propylene, and 1 month after that, a temperature of the heat medium at the entrance was set at a temperature of 335.2° C. At that time, the peak temperature of the catalyst layer was 390° C., a peak position was 220 mm from the entrance of the catalyst layer, a reaction conversion rate of raw material propylene was 98.3%, and a total yield of the acrylic acids and acrolein was 92.6%. In addition, the peak temperature and the peak position of the catalyst layer were calculated, from the maximum temperature of the multipoint thermometer used for the temperature measurement and temperatures measured at positions before and after that position, by use of a quadratic function passing these three points.

On the basis of the condition ($T_0=394°$ C. and $X_0=220$ mm), the operation was continued with the temperature of the heat medium controlling so that the temperature rise of the peak temperature might be in a range of $L\times\{|T-T_0|/(X-X_0)\}=60\pm10$.

After 11 months since the beginning of the operation, a temperature of the heat medium at the entrance was 335.6° C., the peak temperature of the catalyst layer was 392.4° C., the peak position was 320 mm ($L\times\{|T-T_0|/(X-X_0)\}=58$) from the entrance side of the catalyst layer, the reaction conversion rate of raw material propylene was 98.0% and a total yield of acrylic acid and acrolein was 92.2%.

When a continuous operation for 11 months was repeated three times with one-month stop period interposed therebetween, a temperature of the heat medium at the entrance was 337.1° C., the peak temperature of the catalyst layer was 399.5° C., the peak position was 550 mm ($L\times\{|T-T_0|/(X-X_0)\}=58$) from the entrance side of the catalyst layer, the reaction conversion rate of raw material propylene was 97.4% and a total yield of acrylic acid and acrolein was 90.4%.

Comparative Example

An operation of the reactor was begun similarly to the example. After 1 month had passed since the beginning of the operation, a temperature of the heat medium at the entrance was set at a temperature of 335.0° C. At that time, the peak temperature of the catalyst layer was 388° C., the peak position was 230 mm from the entrance of the catalyst layer, the reaction conversion rate of raw material propylene was 98.4% and the total yield of acrylic acid and acrolein was 92.7%.

On the basis of the condition mentioned above ($T_0=388°$ C. and $X_0=230$ mm), the operation was continued with the temperature of the heat medium regulated so that the reaction conversion rate of raw material propylene might be 98.2±0.3%.

After 11 months passed since the beginning of operation, the temperature of the heat medium at the entrance was 336.2° C., the peak temperature of the catalyst layer was 393.0° C., the peak position was 260 mm ($L\times\{|T-T_0|/(X-X_0)\}=580$) from the entrance of the catalyst layer, and the total yield of acrylic acid and acrolein was 91.9%.

Furthermore, after a continuous operation for 11 months was repeated three times with a stop period of 1 month interposed therebetween, the temperature of the heat medium at the entrance was 341.9° C., the peak temperature of the catalyst layer was 405.4° C., the peak position was 240 mm ($L\times\{|T-T_0|/(X-X_0)\}=609$) from the entrance of the catalyst layer, and the total yield of acrylic acid and acrolein decreased to 87.8%.

While the invention has been detailed in detail and with reference to specific embodiments thereof, it will be apparent to one skilled in the art that various changes and modifications can be made therein without departing from the spirit and scope thereof.

This application is based on Japanese patent application (Application No. 2004-108736) filed on Apr. 1, 2004, the entire contents thereof being hereby incorporated by reference.

INDUSTRIAL APPLICABILITY

According to the method of the present invention, without allowing the activity of the catalyst packed in the reaction tubes to decrease enormously, (meth)acrylic acid or (meth)acrolein can be manufactured stably and with high yield.

The invention claimed is:

1. In a method of producing (meth)acrolein or (meth)acrylic acid comprising the gas phase catalytic oxidation of at least one substance selected from the group consisting of propylene, propane, and isobutylene in the presence of molecular oxygen or a gas containing molecular oxygen in a fixed bed multi-tubular reactor having a plurality of reaction tubes, wherein the reaction tubes are filled with at least one catalyst and the reaction temperature is controlled by a heat medium flowing outside of the reaction tubes, the improvement comprising:

(1) said at least one catalyst is a Mo—Bi-based composite oxide catalyst, (2) at the beginning of the reaction process, the temperature difference between a temperature of the heat medium and a peak temperature of the catalyst is set in the range of 20 to 80° C., and (3) during the reaction process, a peak temperature T (° C.) of the catalyst in the tube axis direction of the reaction tubes satisfies Equation 1 below:

$$35 \leq L\times\left(\frac{|T-T_0|}{X-X_0}\right) \leq 300 \qquad \text{(Equation 1)}$$

where L is the length of a reaction tube, $T_0$ is a peak temperature of a catalyst in a tube axis direction at the beginning of the reaction process, X is a length from an entrance of a reaction tube to a position that shows the peak temperature T, and $X_0$ is a length from the entrance of the reaction tube up to a position that shows the peak temperature $T_0$.

2. In a method of producing (meth)acrylic acid comprising the gas phase catalytic oxidation of (meth)acrolein in the presence of molecular oxygen or a gas containing molecular oxygen in a fixed bed multi-tubular reactor having a plurality of reaction tubes, wherein the reaction tubes are filled with at least one catalyst and the reaction temperature is controlled by a heat medium flowing outside of the reaction tubes, the improvement comprising:

(1) said at least one catalyst is a Mo—V-based composite oxide catalyst,
(2) at the beginning of the reaction process, the temperature difference between a temperature of the heat medium and a peak temperature of the catalyst is set in the range of 20 to 80° C., and
(3) during the reaction process, a peak temperature T (° C.) of the catalyst in the tube axis direction of each reaction tube satisfies Equation 1 below:

$$35 \leq L \times \left(\frac{|T - T_0|}{X - X_0}\right) \leq 300 \quad \text{(Equation 1)}$$

where L is the length of a reaction tube, $T_0$ is a peak temperature of a catalyst in a tube axis direction at the beginning of the reaction process, X is a length from an entrance of a reaction tube up to a position that shows the peak temperature T, and $X_0$ is a length from the entrance of the reaction tube up to a position that shows the peak temperature $T_0$.

3. In a method of producing (meth)acrolein or (meth)acrylic acid comprising the gas phase catalytic oxidation of at least one substance selected from the group consisting of propylene, propane, isobutylene and (meth)acrolein in the presence of molecular oxygen or a gas containing molecular oxygen in a fixed bed multi-tubular reactor having a plurality of reaction tubes, wherein the reaction tubes are filled with first and second catalysts in a tube axis direction and the reaction temperature is controlled by a heat medium flowing outside of the reaction tubes, the improvement comprising:
(1) said first catalyst is Mo—Bi-based composite oxide catalyst,
(2) said second catalyst is Mo—V-based composite oxide catalyst,
(3) at the beginning of the reaction process, the temperature difference between a temperature of the heat medium and a peak temperature of the catalyst is set in the range of 20 to 80° C., and
(4) during the reaction process, a peak temperature T (° C.) of the catalyst in the tube axis direction of each reaction tube satisfies Equation 1 below:

$$35 \leq L \times \left(\frac{|T - T_0|}{X - X_0}\right) \leq 300 \quad \text{(Equation 1)}$$

where L is the length of a reaction tube, $T_0$ is a peak temperature of the catalyst in a tube axis direction at the beginning of the reaction process, X is a length from an entrance of a reaction tube up to a position that shows the peak temperature T, and $X_0$ is a length from the entrance of the reaction tube up to a position that shows the peak temperature $T_0$.

4. The improved method of claim 1, wherein the Mo—Bi-based composite oxide catalyst has the formula:

$Mo_aW_bBi_cFe_dA_eB_fC_gD_hE_iO_x$;

where A, B, C, D, E, and O are elements, and
A is at least one of Ni and Co;
B is at least one of Na, K, Rb, Cs, and Tl;
C is at least one alkaline earth metal;
D is at least one of P, Te, Sb, Sn, Ce, Pb, Nb, Mn, As, B, and Zn;
E is at least one of Si, Al, Ti, and Zr; and
O is oxygen;

where a, b, c, d, e, f, g, h, i, and x are atomic ratios, and
a is 12;
0≦b≦10;
0<c≦10;
0<d≦10;
2≦e≦15;
0<f≦10;
0≦g≦10;
0≦h≦4;
0≦i≦30;
x is a value determined by the oxidation state of the respective elements.

5. The improved method of claim 3, wherein the Mo—Bi-based composite oxide catalyst has the formula:

$Mo_aW_bBi_cFe_dA_eB_fC_gD_hE_iO_x$;

where A, B, C, D, E, and O are elements, and
A is at least one of Ni and Co;
B is at least one of Na, K, Rb, Cs, and Ti;
C is at least one alkaline earth metal;
D is at least one of P, Te, Sb, Sn, Ce, Pb, Nb, Mn, As, B, and Zn;
E is at least one of Si, Al, Ti, and Zr; and
O is oxygen;

where a, b, c, d, e, f, g, h, i, and x are atomic ratios, and
a is 12;
0 ≦b≦10;
0 <c≦10;
0 <K≦10;
2 ≦e≦15;
0 ≦f≦10;
0 ≦g≦10;
0 ≦h≦4;
0 ≦i≦30; and
x is a value determined by the oxidation state of the respective elements.

6. The improved method of claim 2, wherein the Mo—V-based composite oxide catalyst has the formula:

$Mo_aV_bW_cCU_dX_eY_fO_g$;

where X, Y, and O are elements, and
X is at least one of Mg, Ca, Sr, and Ba;
Y is at least one of Ti, Zr, Ce, Cr, Mn, Fe, Co, Ni, Zn, Nb, Sn, Sb, Pb, and Bi; and
O is oxygen;

where a, b, c, d, e, f and g are atomic ratios, and
a is 12;
2≦b≦14;
0≦c≦12;
0≦d≦6
0≦e≦3;
0≦f≦3 and
g is a value determined by the oxidation state of the respective elements.

7. The improved method of claim 3, wherein the Mo—V-based composite oxide catalyst has the formula:

$Mo_aV_bW_cCU_dX_eY_fO_g$;

where X, Y, and O are elements, and
X is at least one of Mg, Ca, Sr, and Ba;
Y is at least one of Ti, Zr, Ce, Cr, Mn, Fe, Co, Ni, Zn, Nb, Sn, Sb, Pb, and Bi; and
O is oxygen;

where a, b, c, d, e, f, and g are atomic ratios, and
a is 12;
2≦b≦14;
0≦c≦12;

0≦d≦6
0≦e≦3
0≦f≦3 and
g is a value determined by the oxidation state of the respective elements.

8. The improved method of claim 4, wherein the Mo—Bi-based composite oxide catalyst has the formula:

$Mo_{12}Bi_5Ni_3Co_2Fe_{0.4}Na_{0.2}Mg_{0.4}B_{0.2}K_{0.1}Si_{24}O_x$.

9. The improved method of claim 5, wherein the Mo—Bi-based composite oxide catalyst has the formula:

$Mo_{12}Bi_5Ni_3Co_2Fe_{0.4}Na_{0.2}Mg_{0.4}B_{0.2}K_{0.1}Si_{24}O_x$.

10. The improved method of claim 1, wherein, during the reaction process, a peak temperature T (° C.) of the catalyst in the tube axis direction of each reaction tube satisfies Equation 2 below:

$$40 \leq L \times \{|T-T_0|/(X-X_0)\} \leq 200 \quad \text{(Equation 2)}$$

where L is the length of a reaction tube, $T_0$ is a peak temperature of a catalyst in a tube axis direction at the beginning of the reaction process, X is a length from an entrance of a reaction tube up to a position that shows the peak temperature T, and $X_0$ is a length from the entrance of the reaction tube up to a position that shows the peak temperature $T_0$.

11. The improved method of claim 2, wherein, during the reaction process, a peak temperature T (° C.) of the catalyst in the tube axis direction of each reaction tube satisfies Equation 2 below:

$$40 \leq L \times \{|T-T_0|/(X-X_0)\} \leq 200 \quad \text{(Equation 2)}$$

where L is the length of a reaction tube, $T_0$ is a peak temperature of a catalyst in a tube axis direction at the beginning of the reaction process, X is a length from an entrance of a reaction tube up to a position that shows the peak temperature T, and $X_0$ is a length from the entrance of the reaction tube up to a position that shows the peak temperature $T_0$.

12. The improved method of claim 3, wherein, during the reaction process, a peak temperature T (° C.) of the catalyst in the tube axis direction of each reaction tube satisfies Equation 2 below:

$$40 \leq L \times \{|T-T_0|/(X-X_0)\} \leq 200 \quad \text{(Equation 2)}$$

where L is the length of a reaction tube, $T_0$ is a peak temperature of a catalyst in a tube axis direction at the beginning of the reaction process, X is a length from an entrance of a reaction tube up to a position that shows the peak temperature T, and $X_0$ is a length from the entrance of the reaction tube up to a position that shows the peak temperature $T_0$.

13. The improved method of claim 4, wherein the Mo—Bi-based composite oxide catalyst has the formula:

$Mo_aW_bBi_cFe_dA_cB_fC_gD_hE_iO_x$;

where A, B, C, D, E, and O are elements, and
A is at least one of Ni and Co;
B is at least one of Na, K, Rb, Cs, and Tl;
C is at least one alkaline earth metal;
D is at least one of P, Te, Sb, Sn, Ce, Pb, Nb, Mn, As, B, and Zn;
E is at least one of Si, Al, Ti, and Zr; and
O is oxygen;
where a, b, c, d, e, f, g, h, i, and x are atomic ratios, and
a is 12;
0≦b≦10;
0.1≦c≦10;
0.1≦d≦10;
2≦e≦15;
0.001≦f≦10;
0≦g≦10;
0≦h≦4;
0≦i≦30; and
x is a value determined by the oxidation state of the respective elements.

14. The improved method of claim 5, wherein the Mo—Bi-based composite oxide catalyst has the formula:

$Mo_aW_bBi_cFe_dA_cB_fC_gD_hE_iO_x$;

where A, B, C, D, E, and O are elements, and
A is at least one of Ni and Co;
B is at least one of Na, K, Rb, Cs, and Tl;
C is at least one alkaline earth metal;
D is at least one of P, Te, Sb, Sn, Ce, Pb, Nb, Mn, As, B, and Zn;
E is at least one of Si, Al, Ti, and Zr; and
O is oxygen;
where a, b, c, d, e, f, g, h, i, and x are atomic ratios, and
a is 12;
0≦b≦10;
0.1≦c≦10;
0.1≦d≦10;
2≦e≦15;
0.001≦f≦10;
0≦g≦10;
0≦h≦4;
0≦i≦30; and
x is a value determined by the oxidation state of the respective elements.

15. The improved method of claim 1, wherein the temperature difference between a temperature of the heat medium and a peak temperature of the catalyst is set in the range of 20 to 70° C.

16. The improved method of claim 2, wherein the temperature difference between a temperature of the heat medium and a peak temperature of the catalyst is set in the range of 20 to 70° C.

17. The improved method of claim 3, wherein the temperature difference between a temperature of the heat medium and a peak temperature of the catalyst is set in the range of 20 to 70° C.

18. The improved method of claim 1, wherein the reaction tubes have a length of 3.5 m and an inner diameter of 27 mm.

19. The improved method of claim 2, wherein the reaction tubes have a length of 3.5 m and an inner diameter of 27 mm.

20. The improved method of claim 3, wherein the reaction tubes have a length of 3.5 m and an inner diameter of 27 mm.

* * * * *